United States Patent
Matsuya et al.

(10) Patent No.: US 6,723,997 B2
(45) Date of Patent: Apr. 20, 2004

(54) ABERRATION CORRECTOR FOR INSTRUMENT UTILIZING CHARGED-PARTICLE BEAM

(75) Inventors: Miyuki Matsuya, Tokyo (JP); Kazuhiro Honda, Tokyo (JP)

(73) Assignee: Jeol Ltd., Tokyo (JP)

( * ) Notice: Subject to any disclaimer, the term of this patent is extended or adjusted under 35 U.S.C. 154(b) by 0 days.

(21) Appl. No.: 10/281,378

(22) Filed: Oct. 25, 2002

(65) Prior Publication Data

US 2003/0098415 A1 May 29, 2003

(30) Foreign Application Priority Data

Oct. 26, 2001 (JP) ........................................ 2001-328776

(51) Int. Cl.$^7$ ............................. H01J 3/14; H01J 37/26
(52) U.S. Cl. ......................... 250/396 R; 250/396 ML; 250/305; 250/306; 250/310
(58) Field of Search ....................... 250/396 R, 492.22, 250/492.3, 396 ML

(56) References Cited

U.S. PATENT DOCUMENTS

| | | | |
|---|---|---|---|
| 4,859,857 A | * | 8/1989 | Stengl et al. ............. 250/492.3 |
| 6,525,328 B1 | * | 2/2003 | Miyoshi et al. ......... 250/492.22 |
| 2003/0010926 A1 | * | 1/2003 | Lanio ..................... 250/396 R |

OTHER PUBLICATIONS

"Abbildungseigenschaften sphärisch korrigierter elektronenoptischer Acromate", Von. H. Rose, *Optik 33*, Heft 1, pp. 1–24 (1971).

"Design of a high–resolution low–voltage scanning electron microscope", J. Zach, *Optik 83*, No. 1 (1989), pp. 30–40.

"Aberration correction in low voltage SEM by a multiple corrector", J. Zach et al., *Nucl. Instr. and Meth. in Phys. Res. A 363* (1995), pp. 316–325.

"Design and test of an electric and magnetic dodecapole lens", M. Haider et al., *Optik 63*, No. 1 (1982), pp. 9–23.

* cited by examiner

*Primary Examiner*—John R. Lee
*Assistant Examiner*—James J. Leybourne
(74) *Attorney, Agent, or Firm*—Webb, Ziesenheim Logsdon Orkin & Hanson, P.C.

(57) ABSTRACT

An aberration corrector comprises four stages of electrostatic quadrupole elements, two stages of electrostatic quadrupole elements for superimposing a magnetic potential distribution analogous to the electric potential distribution created by the two central ones of the four stages of the electrostatic quadrupole elements on the electric potential distribution, an objective lens, a manual operation portion permitting a user to modify the accelerating voltage or the working distance, a power supply for supplying voltages to the four stages of electrostatic quadrupole elements, a power supply for exciting the two stages of magnetic quadrupole elements, a power supply for the objective lens, and a control portion for controlling the power supplies according to a manual operation or setting performed on the manual operation portion.

24 Claims, 8 Drawing Sheets

ABERRATION CORRECTOR FOR INSTRUMENT UTILIZING CHARGED-PARTICLE BEAM

BACKGROUND OF THE INVENTION

1. Field of the Invention

The present invention relates to an aberration corrector for use in an instrument (e.g., an instrument using an electron beam or ion beam, such as a scanning electron microscope or ion microprobe) utilizing a charged-particle beam to correct chromatic and spherical aberrations in such an instrument.

2. Description of Related Art

In a scanning electron microscope or transmission electron microscope, an aberration corrector is incorporated in the optics in order to provide high-resolution imaging or enhance the probe current density. One proposed example of this aberration corrector uses a combination of electrostatic quadrupole elements and magnetic quadrupole elements to correct chromatic aberration. The corrector also uses four stages of octupole elements to correct spherical aberration. The principle is introduced in detail in various literature: [1] H. Rose, Optik 33, Heft 1, pp. 1–24 (1971); [2] J. Zach, Optik 83, No. 1, pp. 30–40 (1989); and [3] J. Zach and M. Haider, Nucl. Instru. and Meth. in Phys. Res. A 363, pp. 316–325 (1995).

The principle of the above-described aberration corrector is described briefly now by referring to FIG. 1, where an aberration corrector C is placed ahead of an objective lens 7. The aberration corrector C comprises four stages of electrostatic quadrupole elements 1, 2, 3, 4, two stages of magnetic quadrupole elements 5, 6, and four stages of electrostatic octupole elements 11, 12, 13, 14. The two stages of magnetic quadrupole elements 5, 6 create a magnetic potential distribution analogous to the electric potential distribution created by the second and third stages of the electrostatic quadrupole elements to produce a magnetic field superimposed on the electric field. The four stages of electrostatic octupole elements 11, 12, 13, 14 create an electric field superimposed on the electric field created by the four stages of electrostatic quadrupole elements 1–4.

In an actual instrument, four stages of dipole elements and four stages of hexapole elements are also mounted to produce fields superimposed on the fields created by the aforementioned quadrupole and octupole elements. The dipole elements act as deflecting devices for axial alignment. The hexapole elements act to correct the second-order aperture aberration. Since these dipole and hexapole elements are not closely related to the present invention, they will not be described in detail below.

In this configuration, a beam of charged particles is entered from the left side as viewed in the figure. The four stages of electrostatic quadrupole elements 1–4 and the objective lens 7 together act to form a reference orbit for the beam. As a result, the beam is focused onto a specimen surface 20. In FIG. 1, both orbit $R_x$ of the particle beam in the X-direction and orbit $R_y$ in the Y-direction are schematically drawn on the same plane.

The reference orbit can be regarded as a paraxial orbit, that is, an orbit assumed where there is no aberration. The quadrupole element 1 causes the Y-direction orbit $R_y$ to pass through the center of the quadrupole element 2. The quadrupole element 2 causes the X-direction orbit $R_x$ to pass through the center of the quadrupole element 3. Finally, the quadrupole elements 3, 4 and objective lens 7 together focus the beam onto the specimen surface. In practice, these components need to be adjusted mutually for complete focusing. At this time, the four stages of dipole elements are used for axial alignment.

Referring more particularly to FIG. 1, the charged-particle beam in the X-direction orbit $R_x$ is diverged by the quadrupole element 1 acting like a concave lens. Then, the beam is converged by the quadrupole element 2 acting like a convex lens. The beam is thus made to pass through the center of the quadrupole element 3. Then, the beam is converged by the quadrupole element 4 and travels toward the objective lens 7. On the other hand, the charged-particle beam in the Y-direction orbit $R_y$ is converged by the quadrupole element 1 and made to pass through the center of the quadrupole element 2. Then, the beam is converged by the quadrupole element 3. Finally, the beam is diverged by the quadrupole element 4 and moves toward the objective lens 7. In this way, the function of a single concave lens is created by combining the divergent action of the quadrupole element 1 acting on the X-direction orbit $R_x$ and the divergent action of the quadrupole element 4 acting on the Y-direction orbit $R_y$.

Correction of chromatic aberration using the aberration corrector C is described. To correct chromatic aberration by the system shown in FIG. 1, the potential $\phi_{q2}$ volts at the electrostatic quadrupole element 2 and the magnetic excitation $J_2$ amp turns (or magnetic potential) of the magnetic quadrupole element 5 are adjusted such that the reference orbit is not affected. The whole lens system acts to correct the X-direction chromatic aberration to zero. Similarly, the potential $\phi_{q3}$ volts at the electrostatic quadrupole element 3 and the magnetic excitation $J_3$ amp turns of the magnetic quadrupole element 6 are adjusted such that the reference orbit is not affected. The whole lens system acts to correct the Y-direction chromatic aberration to zero.

Correction of spherical aberration (correction of the third-order aperture aberration) is next described. Before spherical aberration is corrected, X- and Y-direction chromatic aberrations are corrected. Then, the X-direction spherical aberration in the whole lens system is corrected to zero by the potential $\phi_{02}$ volts at the electrostatic octupole element 12. The Y-direction spherical aberration is corrected to zero by the potential $\phi_{03}$ volts at the electrostatic octupole element 13.

Then, the spherical aberration in the resultant direction of the X- and Y-directions is corrected to zero by the electrostatic octupole elements 11 and 14. In practice, repeated mutual adjustments are necessary. Superimposition of the potentials and magnetic excitations at the quadrupole and octupole elements has been put into practical use by varying the potential or excitation applied to each pole of a single twelve-pole element by using this twelve-pole element to synthesize dipoles, quadrupoles, hexapoles, octupoles, etc. This method has been introduced, for example, in [4] M. Haider et al., Optik 63, No. 1, pp. 9–23 (1982).

In particular, in an electrostatic design, a final stage of power supplies $A_n$ (n=1, 2, . . . , 12) capable of supplying a voltage to 12 electrodes $U_n$ (n=1, 2, . . . , 12) independently is connected as shown in FIG. 9 of this patent application. Where a quadrupole field is produced, output voltages from a quadrupole power supply 10 are supplied to the final-stage power supplies $A_n$ to obtain a quadrupole field close to an ideal quadrupole field. If it is assumed that the output voltages from the final-stage power supplies $A_n$ are proportional to the output voltages from the quadrupole power supply 10, the ratio of the output voltages from the power supply 10 assumes a value as given in the reference [4] above. Where an octupole field is created to be superimposed on this quadrupole field, output voltages from an octupole power supply 18 are added to the output voltages from the quadrupole power supply 10 and supplied to the final-stage power supplies $A_n$ to obtain a field close to an ideal octupole field. Similarly, a field on which a multipole field produced by a 2n-pole element (n=1, 2, . . . , 6) is superimposed is obtained using the single twelve-pole element.

In a magnetic design, a final stage of power supplies $B_n$ (n=1, 2, . . . , 12) capable of supplying excitation currents to the coils on 12 magnets $W_n$ (n=1, 2, . . . , 12) independently is connected as shown in FIG. 10 of this patent application. Where a quadrupole magnetic field is created, output voltages from a quadrupole magnetic-field power supply 15 are supplied to the final stage of power supplies $B_n$ to produce a field close to an ideal quadrupole magnetic field. If it is assumed that the output currents from the final-stage power supplies $B_n$ are proportional to the output voltage from the quadrupole magnetic-field power supply 15, the ratio of the output voltages from the power supply 15 assumes a magnetic exciting ratio as given in the reference [4] above. Superimposition of multipole fields other than a quadrupole magnetic field is not explained herein. However, multipole fields other than a quadrupole magnetic field can be superimposed in the same way as in the electrostatic design, by adding voltages for multipole fields to the input voltage to the final-stage power supplies $B_n$. A yoke for magnetically connecting the outside portions of the magnets $W_n$ is omitted in FIG. 10.

Where electrostatic and magnetic designs are superimposed, a conductive magnetic material may be used so that the magnets $W_n$ can act also as the electrodes $U_n$. In this case, the coils on the magnets are mounted so as to be electrically isolated from the electrodes.

In the description given below, the 2n-pole elements are treated as if they were superimposed on top of each other to simplify the explanation. In practice, superimposition of multipole fields on a single twelve-pole field is achieved by adding voltage signals as mentioned previously.

After correction of chromatic aberration, it may be necessary to correct the second-order aperture aberration by means of four stages of hexapole elements before correction of spherical aberration is performed. This correction is made in the same procedure as in the aforementioned correction of spherical aberration. This second-order aperture aberration occurs depending on the mechanical accuracy of the aberration corrector. Normally, the amount of correction is small, and this aberration affects higher-order aberrations only a little within the scope of the present invention. The second-order aperture aberration is corrected within the aberration corrector. If the resultant magnification (described later) of the aberration corrector and the objective lens is varied, higher-order aberrations are affected little, though the resultant magnification is important in the present invention. Therefore, description of the correction of the second-order aperture aberration is omitted herein.

Potential or voltage φ used in the following description regarding electrostatic multipole elements indicates a positive value of the multipole elements arranged normally as shown in FIGS. 2(a) and 2(b). Similarly, magnetic excitation J of magnetic type indicates magnetic excitation amp turns on the positive side.

The aforementioned theory of aberration correction and the results of actually performed experiments demonstrate that chromatic and spherical aberrations are almost completely corrected. This proves the excellence of the aberration correction system described above. From a practical point of view, it can be said that sufficient consideration has not been given to the stability of the aberration correction system and to the range of the applied voltage. Therefore, the following problems have arisen.

First, where the accelerating voltage $V_a$ for a particle probe or the working distance WD indicative of the space between the objective lens 7 and the specimen surface 20 is varied, the magnetic excitation of the magnetic quadrupole is correspondingly varied. Concomitantly, slight magnetic drift δB occurs. Where long-term, high stability is required, this drift may shift the reference orbit for the charged-particle beam and disturb the aberration correction conditions.

Secondly, where the accelerating voltage for the charged-particle beam is low, if the voltage necessary for correction of chromatic and spherical aberrations is set to a higher voltage in some degree, the voltage resistance (or withstand voltage) of the electrostatic multipole elements, such as quadrupole and octupole elements, presents no problems. We have found that where the accelerating voltage is increased, the magnitude of the correcting voltage greatly exceeds the voltage-resistance limit of the multipole elements.

Thirdly, where the accelerating voltage is used over a wide range from low to high voltage, the voltage of the whole system is low at low accelerating voltages. The voltage applied to each electrostatic quadrupole element contains fluctuation component δφ. At lower voltages, a greater portion of this fluctuation component is given to the correcting voltage and deflecting field. Therefore, where long-term stability or high resolution is required, this fluctuation component δφ presents problems.

Fourthly, certain conditions under which the effects of higher-order aberrations remaining left after correction of chromatic and spherical aberrations are minimized have not been taken into consideration. Examples of these higher-order aberrations include fifth-order aperture aberration (i.e., the amount of aberration is in proportion to the fifth power of the angular aperture of the beam impinging on the specimen surface) and the fourth-order aperture and chromatic aberration (i.e., the amount of aberration is in proportion to the product of the third power of the angular aperture of the beam and the energy spread of the beam, namely, the combined aberration of third-order aperture aberration and first-order chromatic aberration).

SUMMARY OF THE INVENTION

In view of the foregoing circumstances, the present invention has been made. It is an object of the present invention to realize an aberration corrector which is for use in an instrument utilizing a charged-particle beam and which can make optimum aberration correction stably over a long term.

An aberration corrector built in accordance with the present invention is incorporated within the optics of an instrument utilizing a charged-particle beam and comprises four stages of electrostatic quadrupole elements, including two central stages of quadrupole elements, two stages of magnetic quadrupole elements for superimposing a magnetic potential distribution analogous to an electric potential distribution created by the two central stages of quadrupole elements on the electric potential distribution, an objective lens for focusing the charged-particle beam onto a specimen, an objective aperture placed in a part of an optical path for the charged-particle beam, a manual operation portion permitting one to modify the accelerating voltage for the charged-particle beam or the working distance between the objective lens and the specimen, and a control portion for controlling the quadrupole elements and the objective lens according to a manual operation or setting performed on the manual operation portion.

In one feature of the present invention, when either the accelerating voltage or the working distance is varied according to a manual operation or setting performed on the manual operation portion, the control portion adjusts (1) the voltages applied to the electrostatic quadrupole elements and the resultant magnification of the fourth stage of electrostatic quadrupole element and the objective lens if the accelerating voltage is varied under conditions where the excitations of the magnetic quadrupole elements are maintained constant and the control portion adjusts (2) the resultant magnification of the fourth stage of electrostatic quadrupole element and the objective lens if the working distance is varied under conditions where the excitations of the magnetic quadrupole elements are maintained constant, whereby chromatic aberration in the optics for the charged-particle beam is corrected.

In another feature of the present invention, when either the accelerating voltage or the working distance is varied according to a manual operation or setting performed on the manual operation portion, the control portion adjusts (1) the voltages applied to the electrostatic quadrupole elements and electrical currents for exciting the magnetic quadrupole elements while maintaining constant the resultant magnification of the fourth stage of electrostatic quadrupole element and the objective lens if the accelerating voltage is varied under conditions where the absolute values of the voltages across the four stages of electrostatic quadrupole elements are substantially uniform and the control portion adjusts (2) the resultant magnification of the fourth stage of electrostatic quadrupole element and the objective lens if the working distance is varied under conditions where the absolute values of the voltages across the four stages of electrostatic quadrupole elements are substantially uniform, whereby chromatic aberration in the optics for the charged-particle beam is corrected.

In another feature of the present invention, when either the accelerating voltage or the working distance is varied according to a manual operation or setting performed on the manual operation portion, the control portion adjusts (1) the voltages applied to the electrostatic quadrupole elements and electrical currents for exciting the magnetic quadrupole elements while maintaining constant the resultant magnification of the fourth stage of electrostatic quadrupole element and the objective lens if the accelerating voltage is varied under conditions where the absolute values of the voltages across the four stages of electrostatic quadrupole elements are substantially uniform and the control portion adjusts (2) the resultant magnification of the fourth stage of electrostatic quadrupole element and the objective lens if the working distance is varied under conditions where the absolute values of the voltages across the four stages of electrostatic quadrupole elements are substantially uniform to thereby minimize the absolute value of the fifth-order aperture aberration or the fourth-order aperture aberration (i.e., combined aberration of third-order aperture aberration and first-order chromatic aberration) is reduced to zero or its absolute value is reduced to a minimum.

In an additional feature of the present invention, there are further provided four stages of electrostatic octupole elements for superimposing an octupole electric potential on the electric potential distribution created by the four stages of electrostatic quadrupole elements and another control portion for controlling the four stages of electrostatic octupole elements according to a manual operation or setting performed on the manual operation portion, whereby spherical aberration can also be corrected.

In still another feature of the present invention, when either the accelerating voltage or the working distance is varied according to a manual operation or setting performed on the manual operation portion, the control portion adjusts (1) the voltages applied to the electrostatic quadrupole elements and the electrical currents for exciting the magnetic quadrupole elements while maintaining constant the resultant magnification of the fourth stage of electrostatic quadrupole elements and the objective lens if the accelerating voltage is varied under conditions where the absolute values of sums of the voltages across the four stages of electrostatic quadrupole elements and voltages across the electrostatic octupole elements respectively superimposed on the first-mentioned voltages are substantially uniform and the control portion adjusts (2) the resultant magnification of the fourth stage of electrostatic quadrupole element and the objective lens if the working distance is varied under conditions where the absolute values of sums of the voltages across the four stages of electrostatic quadrupole elements and voltages across the electrostatic octupole elements respectively superimposed on the first-mentioned voltages are substantially uniform to thereby correct at least one of chromatic and spherical aberrations in the optics for the charged-particle beam.

The present invention also provides an aberration corrector for use in an instrument utilizing a charged-particle beam, the aberration corrector being incorporated in the optics of the instrument, the aberration corrector comprising: four stages of electrostatic quadrupole elements including two central stages of quadrupole elements; two stages of magnetic quadrupole elements for superimposing a magnetic potential distribution analogous to an electric potential distribution created by the two central stages of quadrupole elements on the electric potential distribution; an objective lens for focusing the charged-particle beam onto a specimen; an objective aperture placed in a part of an optical path for the charged-particle beam; an additional lens mounted between a quadrupole element assembly formed by the four stages of electrostatic quadrupole elements and the objective lens; a manual operation portion permitting one to modify the accelerating voltage for the charged-particle beam or the working distance between the objective lens and the specimen; and a control portion for controlling the four stages of electrostatic quadrupole elements, the two stages of magnetic quadrupole elements, the objective lens, and the additional lens according to a manual operation or setting performed on the manual operation portion.

In one feature of this aberration corrector, when either the accelerating voltage or the working distance is varied according to a manual operation or setting performed on the manual operation portion, the control portion adjusts (1) the voltages applied to the electrostatic quadrupole elements and the resultant magnification of the additional lens and the objective lens if the accelerating voltage is varied under conditions where the excitations of the magnetic quadrupole elements are maintained constant and the control portion adjusts (2) the resultant magnification of the additional lens and the objective lens if the working distance is varied under conditions where the excitations of the magnetic quadrupole elements are maintained constant, to thereby correct chromatic aberration in the optics for the charged-particle beam.

In another feature of this aberration corrector, when either the accelerating voltage or the working distance is varied according to a manual operation or setting performed on the manual operation portion, the control portion adjusts (1) the voltages applied to the electrostatic quadrupole elements and electrical currents for exciting the magnetic quadrupole elements while maintaining constant the resultant magnification of the fourth stage of the additional lens and the objective lens if the accelerating voltage is varied under conditions where the absolute values of the voltages across the four stages of electrostatic quadrupole elements are substantially uniform and the control portion adjusts (2) the resultant magnification of the additional lens and the objective lens if the working distance is varied under conditions where the absolute values of the voltages across the four stages of electrostatic quadrupole elements are substantially uniform to thereby correct chromatic aberration in the optics for the charged-particle beam.

In a further feature of this aberration corrector, the control portion sets the electric potentials at the two central stages of electrostatic quadrupole elements for correcting chromatic aberration and the electric potentials at the four stages of electrostatic octupole elements to their preset values, whereby the absolute value of the fifth-order aperture aberration is minimized or the fourth-order combined aperture and chromatic aberration (i.e., combined aberration of third-order aperture aberration and first-order chromatic aberration) is reduced to zero or its absolute value is reduced to a minimum.

Other objects and features of the invention will appear in the course of the description thereof, which follows.

DESCRIPTION OF THE PREFERRED EMBODIMENTS

Figure 3:
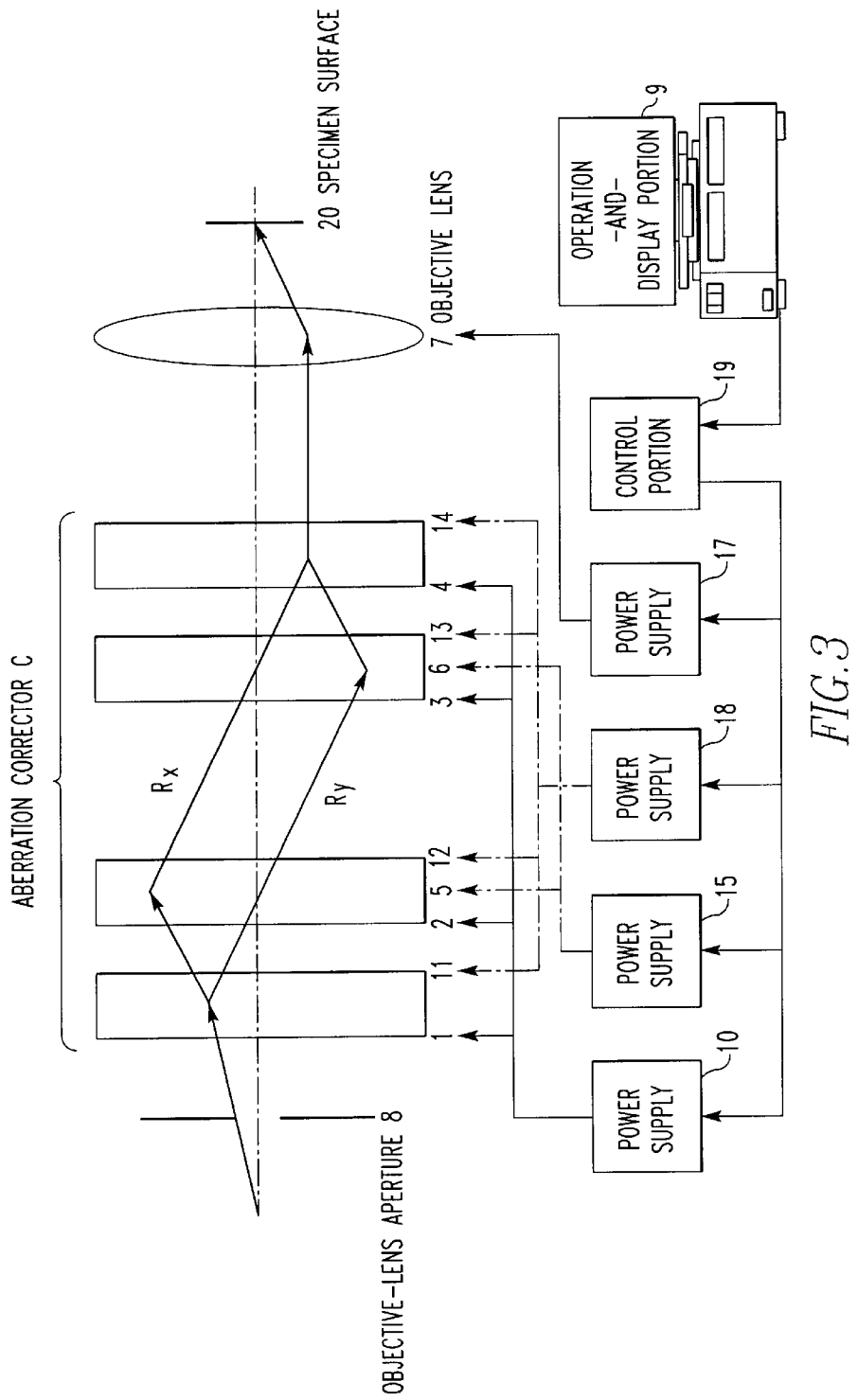
FIG. 3 is a diagram showing the fundamental structure of an aberration corrector according to the present invention.

The preferred embodiments of the present invention are hereinafter described in detail with reference to the accompanying drawings. FIG. 3 shows the fundamental configuration of the present invention. An instrument directs a part of a charged-particle beam as a probe at a specimen. This instrument comprises four stages of electrostatic quadrupole elements 1, 2, 3, 4, two stages of magnetic quadrupole elements 5, 6 for superimposing a magnetic potential distribution analogous to the electric potential distribution created by the two central stages of quadrupole elements 2 and 3, an objective lens 7, an objective aperture 8 placed in a part of the optical path, a manual operation-and-display portion 9 permitting a user to modify the accelerating voltage or the working distance, a power supply 10 for supplying voltages to the four stages of electrostatic quadrupole elements 1–4, a power supply 15 for exciting the two stages of magnetic quadrupole elements 5 and 6, a power supply 17 for the objective lens, and a control portion 19 for controlling the power supplies 10, 15, and 17 according to a manual operation or setting performed on the manual operation-and-display portion 9.

The lens strength is adjusted by varying the current supplied from the power supply 17 where the objective lens 7 is of the magnetic type. The strength is varied by varying the voltage supplied from the power supply 17 where the objective lens 7 is of the electrostatic type. The strength is changed by varying the current and voltage supplied from the power supply 17 where the objective lens 7 is of the electric-magnetic field superimposed type. Where the charged particles are fast ions, an electrostatic objective lens producing the same refractive power regardless of the masses of the charged particles is used as the objective lens 7.

To correct spherical aberration, there are provided four stages of electrostatic octupole elements 11, 12, 13, 14 for superimposing an octupole electric potential on the electric potential distribution created by the four stages of electrostatic quadrupole elements 1, 2, 3, 4, a power supply 18 for supplying voltages to the four stages of electrostatic octupole elements, and the control portion 19 for controlling the power supply 18 according to a manual operation or setting performed on the manual operation-and-display portion 9, in addition to the components described above.

The four stages of electrostatic quadrupole elements 1, 2, 3, 4, two stages of magnetic quadrupole elements 5 and 6, and power supplies 10 and 15 are hereinafter collectively referred to as the aberration corrector C. This corrector C may also contain the four stages of electrostatic octupole elements 11, 12, 13, 14 and power supply 18.

Figure 12:
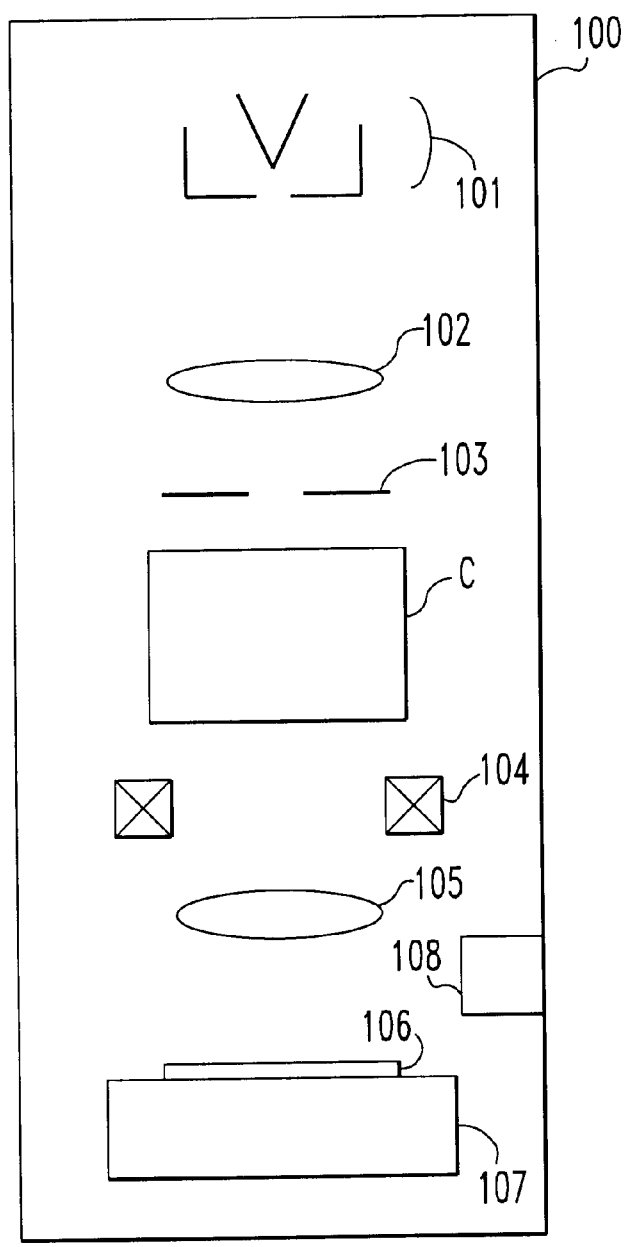
FIG. 12 is a diagram showing an example of scanning electron microscope incorporating an aberration corrector C.

This aberration corrector C is incorporated in a scanning electron microscope or the like as shown in FIG. 12. This scanning electron microscope has a microscope column 100 whose interior is placed in a vacuum environment. Various components are mounted in the microscope column 100 and include an electron gun 101 for producing an electron beam to which energy is given by an accelerating voltage. A condenser lens system 102 converges the electron beam produced by the gun 101 and an objective aperture 103 limits the electron beam current and the angular aperture to an appropriate value. The aberration corrector C is also mounted in the column 100. A deflector 104 deflects and scans the electron beam in two dimensions. An objective lens 105 focuses the beam onto a specimen 106, which is placed on a specimen stage 107. This stage 107 can drive the specimen 106 arbitrarily to permit any desired location of the specimen to be hit and scanned by the electron beam. Concomitantly, secondary electrons and other signals are produced from the specimen 106. These secondary electrons are detected by a detector 108. The components in the range from the electron gun 101 to the objective lens 105 may be referred to or to the specimen 106 with retarding potential as the optics for the electron beam.

A first feature of the present invention is that where the accelerating voltage or working distance is varied through the manual operation-and-display portion 9, the control portion 19 performs the following processing to correct aberrations more stably.

Figure 4:
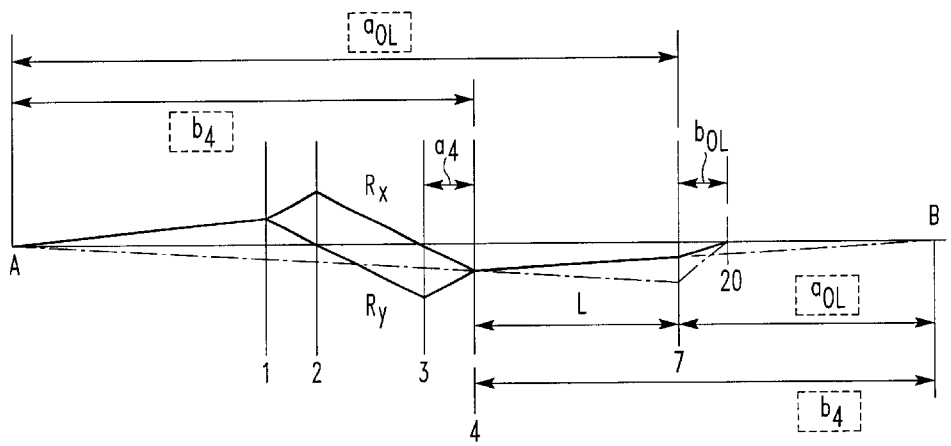
FIG. 4 is a ray diagram illustrating the operating principle of the present invention.
Figure 5:
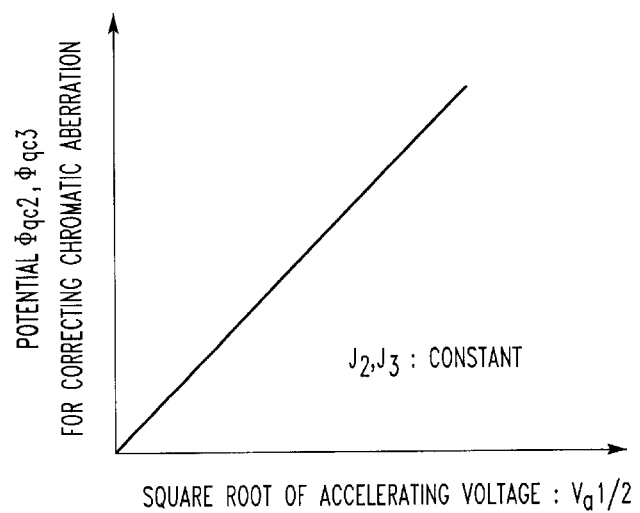
FIG. 5 is a graph showing the relation between accelerating voltage and an aberration correction voltage.

To understand the operating principle of the present invention, correction of chromatic aberration in the X-direction is described by referring to FIGS. 4 and 5 and making a comparison with the simplest relational formula. Let $C_x$ be the chromatic aberration coefficient of the whole lens system satisfying the conditions of the reference orbit provided that chromatic aberration is not corrected.

Figure 8:
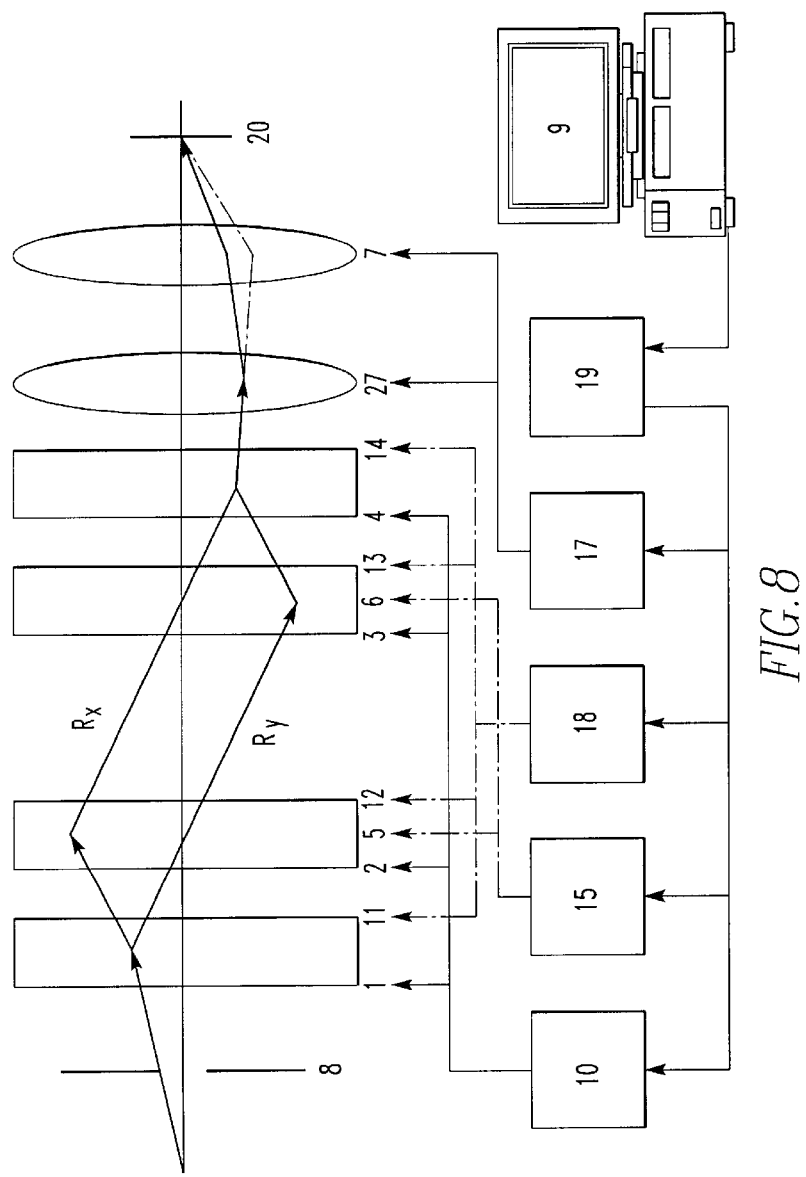
FIG. 8 is a diagram illustrating the manner in which the resultant magnification for chromatic aberration is adjusted by an additional lens.
Figure 9:
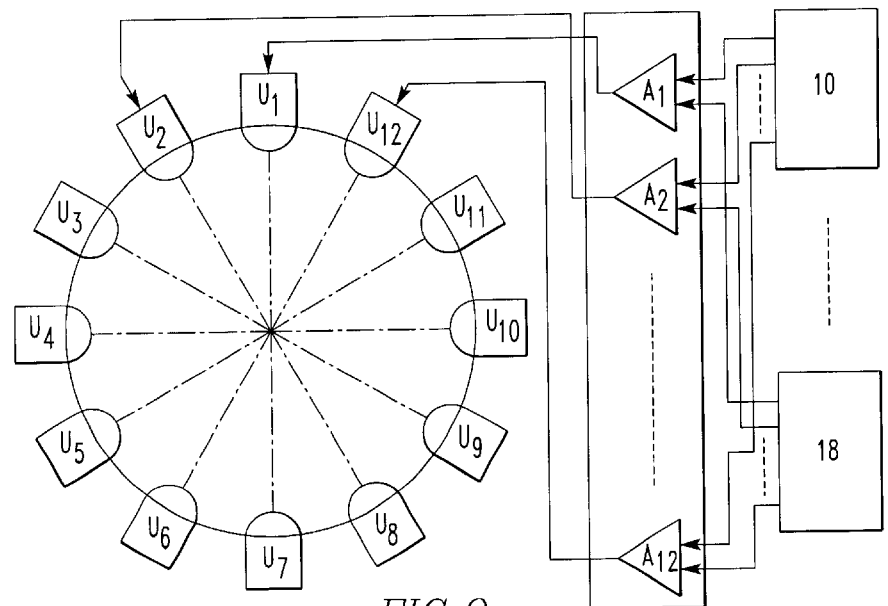
FIG. 9 is a diagram illustrating a method of using an electrostatic 12-pole element as an element having less than 12 poles.
Figure 10:
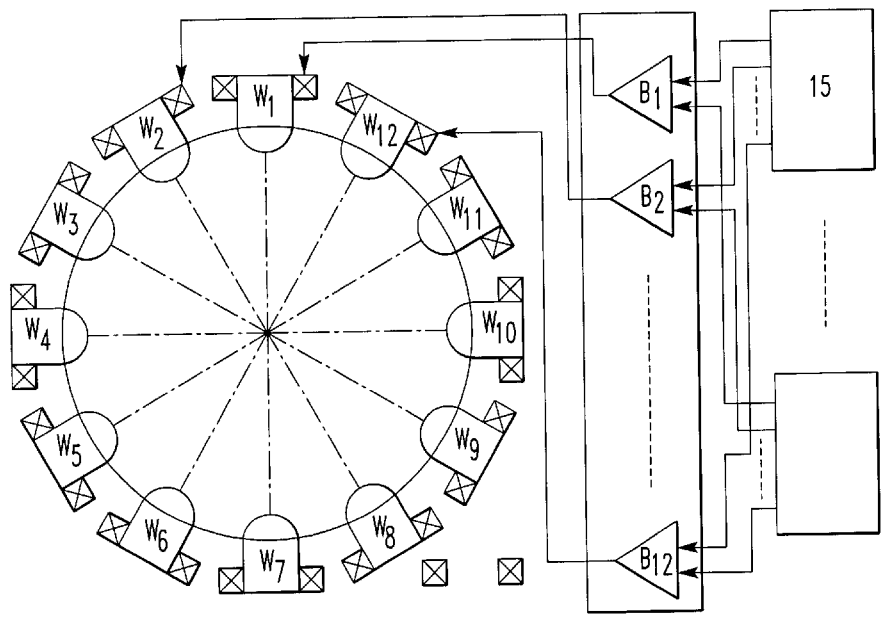
FIG. 10 is a diagram illustrating a method of using an electric field type 12-pole element as an electric field-type element having less than 12 poles.

Simply speaking, the "whole lens system" described above consists of the aberration corrector C and the objective lens 7 in FIG. 3 or the aberration corrector C, an additional lens 27, and the objective lens 7 in FIG. 8. In most instruments, condenser lenses and an extraction electrode acting as lenses are placed ahead of a lens system as shown in FIG. 3 or 8. The extraction electrode is mounted in the source for producing a charged-particle beam. More correctly speaking, the whole lens system includes these condenser lenses and extraction electrode in this case. Alternatively, the whole lens system may include the electron optical system ranging from the electron gun 101 to the objective lens 105 or to the specimen 106 with retarding potential shown in FIG. 12.

The second stage of electrostatic quadrupole element 2 is at focus potential $\phi_{qf2}$. When a voltage of $\phi_{qc2}$ for correction of chromatic aberration is added to this potential, the magnetic excitation $J_2$ of the magnetic quadrupole element 5 for maintaining the reference orbit is given by Eq. (1) provided that the accelerating voltage is constant $$J_2 = k_1 \cdot \phi_{qc2} \quad (1)$$

where $k_1$ is a proportional constant.

The negative chromatic aberration coefficient $C_{cx}$ formed at the specimen surface 20 by the electrostatic quadrupole element 2 and magnetic quadrupole element 5 is given by $$C_{cx} = k_2 \cdot J_2 \quad (2)$$

Since this relation is present, the potential $\phi_{qc2}$ at the electrostatic quadrupole element 2 and the magnetic excitation $J_2$ of the magnetic quadrupole element 5 are adjusted such that the reference orbit remains unchanged before and after aberration correction. Chromatic aberration can be corrected on the assumption $$C_x + C_{cx} = 0 \quad (3)$$

It can be seen that where the accelerating voltage $V_a$ is varied, correction of chromatic aberration is performed without varying the reference orbit by using the simplest relational equations and establishing the following relations within the realm of scanning electron microscopy where the relativistic effect is small:

$$\phi_{qf2} \propto V_a \quad (4\text{-}1)$$

$$\phi_{qc2} \propto V_a \quad (4\text{-}2)$$

$$J_2 \propto V_a^{1/2} \quad (4\text{-}3)$$

Further analysis of the correction of chromatic aberration reveals that a negative aberration coefficient $C_{ox}$ for correcting chromatic aberration is formed at the center of the third stage of electrostatic quadrupole element 3 and magnetic quadrupole element 6 by the second stage of electrostatic quadrupole element 2 and magnetic quadrupole element 5. This negative aberration coefficient is formed at the specimen surface as given by Eq. (5) by the magnification $M_4$ of the fourth stage of electrostatic quadrupole element 4 and the magnification $M_{OL}$ of the objective lens 7.

$$C_{cx} = C_{ox} \cdot (M_4 \cdot M_{OL})^2 \quad (5)$$

In particular, if the potential $\phi_{qc2}$ at the second stage of electrostatic quadrupole element 2 and the magnetic excitation $J_2$ of the magnetic quadrupole element 5 are constant, the amount of aberration correction $C_{cx}$ can be modified by adjusting the resultant magnification $(M_4 \cdot M_{OL})$ of the fourth stage of electrostatic quadrupole element 4 and objective lens 7. In other words, the negative chromatic aberration coefficient $C_{ox}$ can be set to a smaller value by increasing the resultant magnification of the fourth stage of electrostatic quadrupole element 4 and objective lens 7 for the same amount of aberration correction $C_{cx}$. That is, the potential $\phi_{qc2}$ at the electrostatic quadrupole element 2 and the magnetic excitation $J_2$ of the magnetic quadrupole element 5 can be set to smaller values.

Where the magnetic excitations $J_1$ and $J_2$ of the magnetic quadrupole elements are kept constant and the accelerating voltage $V_a$ is varied, in order to maintain the reference orbit $R_x$ in the X-direction unchanged, the electric potentials $\phi_{qc2}$ and $\phi_{qc3}$ for aberration correction are made proportional to the square root of the accelerating voltage as shown in FIG. 5.

The variable range of the resultant magnification is next described in detail. Referring to FIG. 4, let $a_4$ be the distance from the fourth stage of electrostatic quadrupole element 4 to an object. Let $b_4$ be the distance to the image. The distance $a_4$ varies only a little, whether the focal point of the fourth stage of electrostatic quadrupole element 4 is on the side of the charged particle source A or on the side of the specimen surface B. Therefore, the absolute value $M_4$ of the magnification of the fourth stage of electrostatic quadrupole element 4 is given by $$M_4 = \frac{b_4}{a_4} \quad (6)$$

Let L be the distance between the fourth stage of electrostatic quadrupole element 4 and the objective lens 7. Let $b_{OL}$ be the distance between the objective lens 7 and the specimen surface 20. The distance $a_{OL}$ from the objective lens 7 to the object varies depending on the focal point of the fourth electrostatic quadrupole element 4. Where the focal point of the fourth stage of electrostatic quadrupole element 4 is on the side of the specimen surface B, the magnification $M_{OL}$ of the objective lens 7 is given by $$M_{OL} = \frac{b_{OL}}{b_4 - L} \quad (7\text{-}1)$$

Where the focal point of the fourth stage of electrostatic quadrupole element 4 is on the side of the charged particle source A, the magnification $M_{OL}$ of the objective lens 7 is given by $$M_{OL} = \frac{b_{OL}}{b_4 + L} \quad (7\text{-}2)$$

We now introduce a numerical example: $b_4$=244 mm and L=200 mm. The magnification $M_{OL}$ differs by a factor of 10 between them. Thus, it can be seen that the resultant magnification of the fourth stage of quadrupole element 4 and objective lens 7 can be easily varied by at least one order of magnitude. Consequently, for the same potential $\phi_{qc2}$ at the electrostatic quadrupole element 2 and for the same magnetic excitation $J_2$ of the magnetic quadrupole element 5, the chromatic aberration coefficient $C_{cx}$ used for correction can be varied by two or more orders of magnitude.

For the same chromatic aberration coefficient $C_{cx}$, the chromatic aberration coefficient $C_{ox}$ used for correction may be varied by two or more orders of magnitude. Correspondingly, for the same chromatic aberration coefficient $C_{cx}$, the potential $\phi_{qc2}$ at the electrostatic quadrupole element 2 and the magnetic excitation $J_2$ of the magnetic quadrupole element 5 can be varied by two or more orders of magnitude.

The aforementioned theory can be similarly applied to chromatic aberration in the Y-direction. Furthermore, the theory is applicable to aberration coefficient $C_{sox}$ used for correction of X-direction spherical aberration formed at the center of the electrostatic quadrupole element 3 and to spherical aberration in the Y-direction. In the case of spherical aberration, the spherical aberration coefficient formed on the object side is formed on the specimen surface side in proportion to the fourth power of the resultant magnification, i.e., $(M_4 \cdot M_{OL})^4$.

The operation of the aberration corrector for correcting aberrations in accordance with the present invention is next described in detail. The present invention is implemented based on the principle described above. The operation is now described by referring to FIGS. 6(a) and 6(b). To operate the instrument according to the purpose, the corrector can be preferably switched between the following two modes of operation. In a first mode (1), the aberration corrector C is operated while maintaining constant the magnetic excitation $J_2$ of the magnetic quadrupole element 5 and magnetic excitation $J_3$ of the magnetic quadrupole element 6. In a second mode (2), the aberration corrector C is operated such that the absolute values of the voltages across the various electrostatic quadrupole elements are substantially uniform.

Where the first mode is selected through the manual operation-and-display portion 9, i.e., the magnetic excitation $J_2$ of the magnetic quadrupole element 5 and magnetic excitation $J_3$ of the magnetic quadrupole element 6 are maintained constant, even if the accelerating voltage $V_a$ or working distance WD is varied through the use of the manual operation-and-display portion 9, the control portion 19 instructs the power supply 15 for the magnetic quadrupole elements to excite the magnetic quadrupole elements 5 and 6 with constant values given by $$J_2 = J_{20} \quad (8\text{-}1)$$

$$J_3 = J_{30} \quad (8\text{-}2)$$

Under these excitation conditions, in order to obtain a reference orbit focused onto the specimen surface at the presently set accelerating voltage $V_a = V_{a0}$, the control portion 19 causes the electrostatic quadrupole power supply 10 to apply the sum of the potential $\phi_{qf2}$ assumed when chromatic aberration is not corrected and the potential $\phi_{qc2}$ used for correction of chromatic aberration to the electrostatic quadrupole element 2. The control portion 19 also causes the power supply to apply the sum of the potential $\phi_{qf3}$ assumed when chromatic aberration is not corrected and the potential $\phi_{qc3}$ used for correction of chromatic aberration to the electrostatic quadrupole element 3. As a result, the potentials at the electrostatic quadrupole elements 2 and 3 are respectively given by $$\phi_{qf2} + \phi_{qc2} \quad (9\text{-}1)$$

$$\phi_{qf3} + \phi_{qc3} \quad (9\text{-}2)$$

Figure 6A:
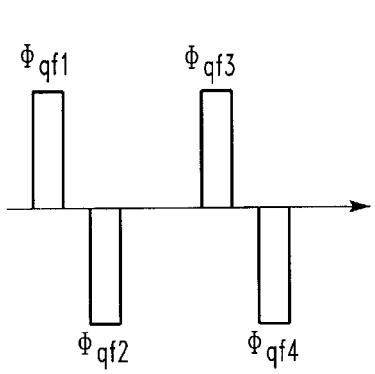
FIGS. 6(a) and 6(b) are diagrams illustrating the electric potentials at electrostatic quadrupole elements before and after correction of chromatic aberration.
Figure 6B:
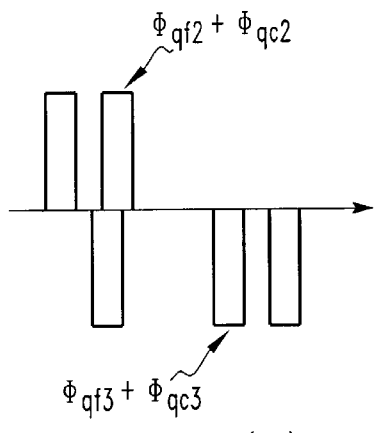

FIG. 6(a) shows the potentials at the electrostatic quadrupole elements assumed before correction of chromatic aberration. FIG. 6(b) shows the potentials at the quadrupole elements assumed after correction of chromatic aberration.

At this time, the control portion 19 controls the power supply 10 for the fourth stage of electrostatic quadrupole element 4 and the power supply 17 for the objective lens 7 by adjusting the resultant magnification of the fourth stage of quadrupole element 4 and objective lens 7 such that the following relations are satisfied:

$$C_x + C_{cx} \approx 0 \quad (10\text{-}1)$$

$$C_y + C_{cy} \approx 0 \quad (10\text{-}2)$$

where $C_x$ is the aberration coefficient in the X-direction of the whole lens system before correction of chromatic aberration, $C_y$ is the aberration coefficient in the Y-direction of the whole lens system before correction of chromatic aberration, $C_{cx}$ is an aberration coefficient formed at the specimen surface 20 for correction by the magnetic excitation $J_2$ and potential $\phi_{qc2}$, and $C_{cy}$ is an aberration coefficient formed at the specimen surface 20 for correction by the magnetic excitation $J_3$ and potential $\phi_{qc3}$.

Where the accelerating voltage $V_a$ is varied through the manual operation-and-display portion 9, the control portion 19 controls the power supply 10 for the electrostatic quadrupole elements to maintain the particle probe focused onto the specimen surface. For this purpose, with respect to the X-direction, the focus potential $\phi_{qf2}$ at the electrostatic quadrupole element 2 and potential $\phi_{qc2}$ for correction of chromatic aberration are controlled such that $$\phi_{qf2} \propto V_a \quad (11\text{-}1)$$

$$\phi_{qc2} \propto V_a^{1/2} \quad (11\text{-}2)$$

With respect to the Y-direction, the control portion 19 similarly controls the power supply 10 for the electrostatic quadrupole elements such that $$\phi_{qf3} \propto V_a \quad (11\text{-}3)$$

$$\phi_{qc3} \propto V_a^{1/2} \quad (11\text{-}4)$$

In consequence, chromatic aberration can be corrected almost to zero by adjusting the total magnification $M_t$ of the lens system while maintaining substantially constant the excitations of the magnetic quadrupole elements.

The "total magnification $M_t$ of the lens system" referred to herein is the magnification of the system including both the whole aberration corrector C and the objective lens 7 in the case of FIG. 3. The magnification $M_4$ of the fourth stage of electrostatic quadrupole element 4 was defined in the description of the resultant magnification ($M_4 \cdot M_{OL}$) of the electrostatic quadrupole element 4 and objective lens 7 in connection with FIG. 4. In a general multipole element, if treated differently between X- and Y-directions, the "magnification" can be defined similarly to a normal lens. Accordingly, the magnification of each multipole element of the aberration corrector C can be defined similarly. The magnification of the whole aberration corrector C can also be defined. The "magnification of the whole aberration corrector C" in the total magnification $M_t$ of the lens system is used in this meaning.

The concept of the "resultant magnification of the electrostatic quadrupole element 4 and objective lens 7" already described in connection with FIG. 4 arises from maximum simplification of the operation, which was made to facilitate understanding the operation of the present invention. In actual operation, however, if this resultant magnification is adjusted, the other quadrupole elements will be affected slightly. Therefore, slight readjustment is necessary. Accordingly, where the actual operation is expressed strictly, it is necessary to adjust the total magnification $M_t$ of the lens system including the whole aberration corrector C and objective lens 7, as well as the resultant magnification of the electrostatic quadrupole element 4 and objective lens 7. In this meaning, "adjustment of the resultant magnification of the electrostatic quadrupole element 4 and objective lens 7" should be more correctly referred to as "adjustment of the total magnification $M_t$ of the lens system".

Where the resultant magnification of the electrostatic quadrupole element 4 and objective lens 7 is varied, the angular aperture of the particle beam hitting the specimen surface changes. This change can be set to an optimum value by placing an angular aperture control lens behind the objective aperture 8 or varying the diameter of the hole in the objective aperture 8.

Where the angular aperture is set optimally ($\alpha = \alpha_0$) at a reference accelerating voltage $V_a = V_{a0}$, if the accelerating voltage $V_a$ is set to a low value, correction of chromatic aberration is performed in such a way that the resultant magnification is suppressed to prevent the necessary amount of aberration correction from becoming excessive. For this reason, the angular aperture $\alpha$ increases.

On the other hand, the optimum angular aperture tends to increase where the accelerating voltage $V_a$ is set to a lower value. Consequently, where the angular aperture is varied by modification of the accelerating voltage in the present invention, the operation is affected favorably.

Where the working distance WD is set larger than the reference value WD=$WD_0$, correction of chromatic aberration is so performed that the resultant magnification is increased to secure the necessary amount of aberration correction. Therefore, the angular aperture $\alpha$ decreases. Where the working distance WD is increased, the optimum angular aperture tends to decrease. In this case, too, where the angular aperture is varied by modification of the working distance in the present invention, the operation is affected favorably. This is described briefly below.

After correcting chromatic and spherical aberrations, diffraction effects and the fifth-order aperture aberration remain. A probe diameter $d_\lambda$ depends on the left diffraction effects, which, in turn, are dependent on the wavelength $\lambda$ of the particle beam. A probe diameter $d_{c5}$ depends on the left fifth-order aperture aberration coefficient $C_5$. It is assumed that these probe diameters $d_\lambda$ and $d_{c5}$ are prevalent. In the least confusion disk, these can be estimated using $$d_\lambda = \frac{1.22\lambda}{\alpha} \tag{12-1}$$

$$d_{c5} = \left(\frac{2}{3}\right) \cdot C_5 \cdot \alpha^5 \tag{12-2}$$

Therefore, the probe diameter $d_p$ represented in terms of a root mean square is given by $$d_p = (d_\lambda^2 + d_{c5}^2)^{1/2} \tag{12-3}$$

Accordingly, from condition $$\frac{\partial d_p}{\partial \alpha} = 0 \tag{12-4}$$

$$\text{we have } \alpha = (1.22\lambda)^{1/6} \cdot \left(\frac{1.5}{5^{1/2} \cdot C_5}\right)^{1/6} \tag{12-5}$$

That is, where the accelerating voltage $V_a$ is low and the wavelength $\lambda$ is large, the optimum angular aperture $\alpha$ is large. Where the working distance WD is increased and thus the fifth-order aperture aberration coefficient is increased, the optimum angular aperture $\alpha$ decreases.

Where the accelerating voltage $V_a$ is lowered, the variations of the potentials at the electrostatic quadrupole elements 2 and 3 which are necessary at least for correction of chromatic aberration are in proportion to $V_a^{1/2}$, because in the selected mode, the excitation currents through the magnetic quadrupole elements necessary for correction of chromatic aberration are constant. Consequently, the operation is less affected by variations in the excitation of the power supply 15 and by the variations in the voltage of the power supply 10 than a normal system where the excitation for correction of chromatic aberration is in proportion to $V_a^{1/2}$ and the electric potential is in proportion to $V_a$.

A case in which the working distance WD is varied is next described. When the working distance is varied through the manual operation-and-display portion 9, the control portion 19 adjusts the focus principally through the electrostatic quadrupole element 4 and objective lens 7 according to the setting. The chromatic aberrations $C_x$ and $C_y$ of the whole lens system to be corrected vary greatly with the working distance WD. As mentioned previously, it is obvious that the necessary chromatic aberrations $C_{cx}$ and $C_{cy}$ to be corrected are obtained at the specimen surface by adjusting the resultant magnification of the electrostatic quadrupole element 4 and objective lens 7.

Similarly, permanent magnets can be used as the magnetic quadrupole elements, because correction of chromatic aberration can be performed while the excitations of the magnetic quadrupole elements 5 and 6 are kept constant as described previously.

The operations described above are summarized now. In the first mode (1), the aberration corrector C is operated while maintaining constant the excitation $J_2$ of the magnetic quadrupole element 5 and excitation $J_3$ of the magnetic quadrupole element 6. If the accelerating voltage is varied after making correction of chromatic aberration at some accelerating voltage and at some working distance, (a) the potentials at the electrostatic quadrupole elements 2 and 3 for correction of chromatic aberration are adjusted in proportion to $V_a^{1/2}$ when chromatic aberration increases or decreases as a result of a modification of the accelerating voltage $V_a$. Furthermore, chromatic aberration is corrected by modifying the resultant magnification of the electrostatic quadrupole element 4 and objective lens 7. Since the excitations of the magnetic quadrupole element are kept constant, it follows that the potentials at the electrostatic quadrupole elements are made proportional to $V_a^{1/2}$. Therefore, the resultant magnification is varied to prevent the amount of correction made to chromatic aberration from becoming excessive or insufficient. At the same time, the state of focus varies with varying the accelerating voltage $V_a$. Correspondingly, the focus potentials at the electrostatic quadrupole elements 1–4 are adjusted in proportion to the accelerating voltage $V_a$. The focus is adjusted while the objective lens 7 maintains the readjusted resultant magnification of the electrostatic quadrupole element 4 and objective lens 7 as mentioned previously. (b) Where the working distance WD is varied, chromatic aberration increases or decreases. In response to this, the resultant magnification of the electrostatic quadrupole element 4 and objective lens 7 is adjusted. Of course, the focus on the specimen must be maintained at this time.

Correction of spherical aberration is performed after this correction of chromatic aberration. The control portion 19 controls the power supply 18 to excite the electrostatic octupole elements 11, 12, 13, and 14 as in the prior art technique according to an instruction from the manual operation-and-display portion 9. The difference with the prior art technique is that it is not necessary to increase the potentials at the electrostatic octupole elements immensely if spherical aberration is increased greatly due to increase of the working distance, because the resultant magnification of the electrostatic quadrupole element 4 and objective lens 7 is matched to correction of chromatic aberration.

In addition, when the accelerating voltage is lowered, decrease of the voltage used to correct spherical aberration is suppressed. The instrument is less affected by variations or fluctuations in the power supply 18.

In the embodiment described thus far, a method in which the excitations of the magnetic quadrupole elements 5 and 6 are kept almost constant has been described. A second embodiment in which the absolute values of the voltages across the electrostatic quadrupole elements are substantially uniform is described. It is assumed that potentials $\phi_{qc2}$ and $\phi_{qc3}$ are added through the manual operation-and-display portion to the potentials $\phi_{qf1}$, $\phi_{qf2}$, $\phi_{qf3}$, and $\phi_{qf4}$ at the electrostatic quadrupole elements 1–4 for creating a reference orbit.

If these corrective potentials are added in the direction to correct chromatic aberration, they are opposite in sign to the potentials $\phi_{qf2}$ and $\phi_{qf3}$ necessary to create the reference orbit as shown in FIGS. 6(a) and 6(b). FIG. 6(a) shows the potentials at the quadrupole elements prior to correction of chromatic aberration. FIG. 6(b) shows the potentials at the quadrupole elements after the correction. Accordingly, the potentials $\phi_{qc2}$ and $\phi_{qc3}$ are set within ranges in which the absolute values of sums given by $$|\phi_{qf2}+\phi_{qc2}| \tag{13-1}$$

$$|\phi_{qf3}+\phi_{qc3}| \tag{13-2}$$

are comparable to the minimum potentials given by $$|\phi_{qf1}| \tag{13-3}$$

$$|\phi_{qf4}| \tag{13-4}$$

which are necessary to create the reference orbit.

Under this condition, the excitations of the magnetic quadrupole elements 5 and 6 producing the reference orbit are determined. Therefore, chromatic aberration can be corrected by adjusting the resultant magnification of the electrostatic quadrupole element 4 and objective lens 7. The same theory can be applied to correction of spherical aberration coefficient.

In the mode where the absolute values of the voltages across the electrostatic quadrupole elements are substantially uniform, the voltage resistances of at least certain electrodes present no problems. Therefore, a maximum accelerating voltage at which aberration correction is permitted can be set to a larger value. In the embodiment described previously in connection with FIGS. 3–5, the excitations $J_2$ and $J_3$ of the magnetic quadrupole elements 5 and 6 are determined to satisfy this condition at the maximum accelerating voltage $V_a$ at which aberration correction is possible.

This second embodiment is also used where the control of the lens system is made simpler. That is, where the accelerating voltage is lowered, the resultant magnification of the electrostatic quadrupole element 4 and objective lens 7 is kept constant. Using the above-described simplest relational formulas, the relations are introduced:

$$\phi_{qf2} \propto V_a \tag{14-1}$$

$$\phi_{qc2} \propto V_a \tag{14-2}$$

$$J_2 \propto V_a^{1/2} \tag{14-3}$$

Moreover, the present invention can also be applied to the case where the working distance WD is increased. That is, when the working distance WD is increased, chromatic aberration coefficient and spherical aberration coefficient increase concomitantly. As a result, these coefficients assume large values. The chromatic aberration coefficient is approximately proportional to the focal length f of the lens. The spherical aberration coefficient is approximately proportional to the third power of the focal distance f. Therefore, the voltages across the electrostatic quadrupole elements 1–4 and octupole elements 11–14 that correct these aberration coefficients assume large values.

The resultant magnification of the electrostatic quadrupole element 4 and the objective lens 7 is varied. The resultant magnification is increased to such an extent that the potential at the electrostatic octupole element for correcting spherical aberration becomes sufficiently small compared with the potential for correcting chromatic aberration. As described previously, the absolute values of the sums of voltages across the electrostatic quadrupole and octupole elements are made almost uniform on the electrodes of an actually used electrostatic multipole element (e.g., 12-pole element). If the accelerating voltage is high, the problem of the voltage resistance of the multipole element is reduced. Under this condition, chromatic and spherical aberrations can be corrected.

In addition, being made almost uniform, the absolute values of the sums of voltages can be made as high as possible while the electrostatic multipole elements can withstand those voltages. That is to say, every absolute value is set at a value between the maximum-withstand voltage and 70%–80% of it, for example. When the accelerating voltage is lowered, decrease of the voltage used to correct aberration is suppressed. The instrument is less affected by variations or fluctuations in the power supplies.

Figure 11A:
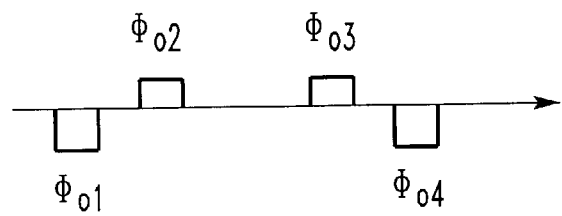
FIGS. 11(a) and 11(b) are diagrams illustrating the electric potentials at an electrostatic octupole element for correction of spherical aberration and the electric potentials at an electrostatic multipole element after correction of chromatic and spherical aberrations.
Figure 11B:
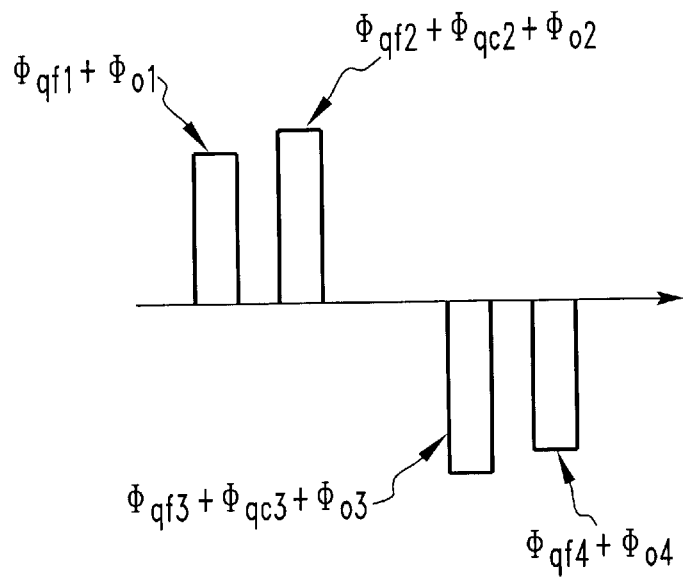

Let $\phi_{o1}$ to $\phi_{o4}$ be the potentials at the first through fourth stages, respectively, of electrostatic octupole elements for correcting spherical aberration. The magnitudes of these potentials can be set to values sufficiently small compared with focus potentials $\phi_{qf1}$ to $\phi_{qf4}$ at the electrostatic quadrupole elements and chromatic aberration-correcting potentials $\phi_{qc2}$ and $\phi_{qc3}$ as shown in FIG. 11(*a*). Therefore, the voltages across the electrodes for the electrostatic multipole elements after correction of chromatic and spherical aberrations are roughly $$|\phi_{qf1}+\phi_{O1}| \tag{15-1}$$

$$|\phi_{qf2}+\phi_{qc2}+\phi_{O2}| \tag{15-2}$$

$$|\phi_{qf3}+\phi_{qc3}+\phi_{O3}| \tag{15-3}$$

$$|\phi_{qf4}+\phi_{O4}| \tag{15-4}$$

If the values of the potentials $\phi_{O1}$ to $\phi_{O4}$ are small, the absolute values of the aforementioned four values can be made comparable to each other. Note that accurate electrode voltages are different according to the number of poles of a multipole element (e.g., a 12-pole element) actually used as an electrostatic quadrupole element or electrostatic octupole element.

The above-described operations are summarized now. In the second mode (2), the aberration corrector C is so operated that the absolute values of the voltages across the electrostatic quadrupole elements are substantially uniform. At some accelerating voltage and at some working distance, chromatic aberration is corrected. If the accelerating voltage is then modified, (a) the potentials at the electrostatic quadrupole elements 2 and 3 for correction of chromatic aberration are adjusted in proportion to $V_a$ when chromatic aberration increases or decreases as a result of a modification of the accelerating voltage $V_a$. The excitations $J_2$ and $J_3$ of the magnetic quadrupole elements 5 and 6 are adjusted in proportion to $V_a^{1/2}$. At the same time, the state of focus varies with varying the accelerating voltage $V_a$. Correspondingly, the focus potentials at the electrostatic quadrupole elements 1–4 are adjusted in proportion to the accelerating voltage $V_a$. The focus is adjusted while the objective lens 7 maintains constant the resultant magnification of the electrostatic quadrupole element 4 and objective lens 7. (b) Where the working distance WD is varied, chromatic aberration increases or decreases. In response to this, the resultant magnification of the electrostatic quadrupole element 4 and objective lens 7 is adjusted. Of course, the focus on the specimen must be maintained at this time.

Figure 7:
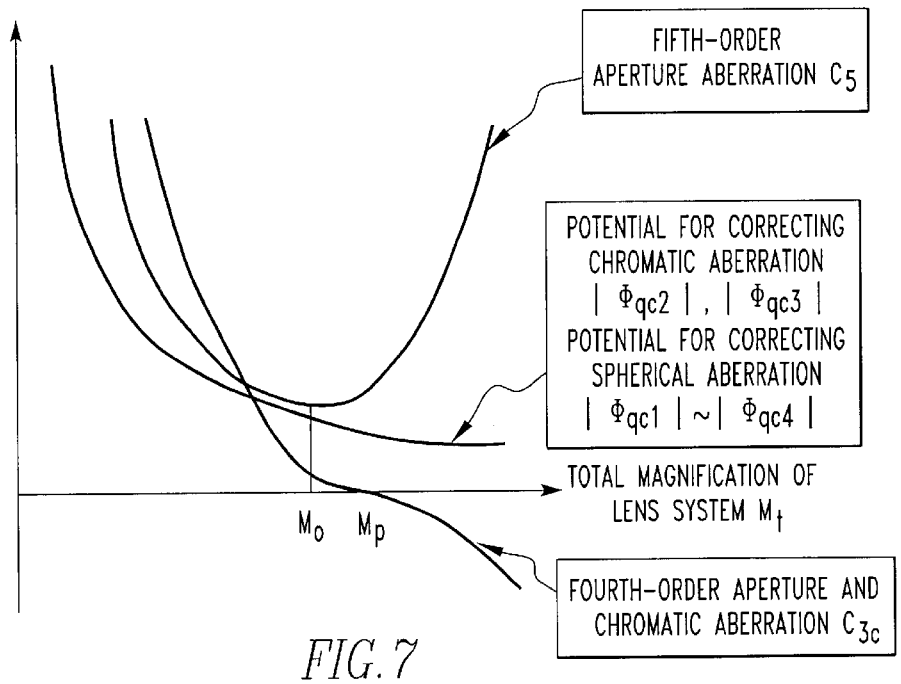
FIG. 7 is a graph showing the manner in which the fifth-order aperture aberration and the fourth-order aperture chromatic aberration are reduced.

The above-described first and second modes are described in further detail. In the first mode (1), the aberration corrector C is operated while maintaining constant the excitation $J_2$ of the magnetic quadrupole element 5 and excitation $J_3$ of the magnetic quadrupole element 6. In the second mode (2), the aberration corrector C is so operated that the absolute values of the voltages across the electrostatic quadrupole elements are substantially uniform. The usage of these two modes is described further. Generally, the first mode is used where the accelerating voltage is relatively low. The second mode is used where the voltage is relatively high.

Where chromatic and spherical aberrations are corrected, (i) diffraction aberration dependent on the wavelength of the particle beam and (ii) fifth-order aperture aberration intrinsic in the lens system are prevalent among factors determining the minimum probe diameter. When the total magnification $M_t$ of the lens system shown in FIG. 3 is varied, for example, by varying the resultant magnification of the electrostatic quadrupole element 4 and objective lens 7, calculation has demonstrated that there is a magnification $M_t=M_O$ at which the absolute value of the fifth-order aperture aberration coefficient converted onto the specimen surface is minimized under conditions close to the conditions of the second embodiment. FIG. 7 shows the manner in which the fifth-order aperture aberration coefficient $C_5$ and fourth-order combined aberration coefficient $C_{3c}$ decrease.

In the example of FIG. 7, the accelerating voltage and the working distance are kept constant. As is clear from the description provided above, there are innumerable combinations of conditions under which the aberration corrector C is set and values of the total magnification (or resultant magnification) of the lens system in the method according to the present invention. That is, in the method, the conditions under which the aberration corrector C is set are appropriately set. Chromatic aberration is corrected by varying the "resultant magnification" and spherical aberration is corrected by adjusting the octopole potentials. The purpose is achieved at whatever combination as long as only correction of chromatic and spherical aberrations is taken into consideration. However, where it is necessary to take account of the fifth-order aperture aberration and fourth-order combined aberration of aperture and chromatic aberration as well, the total magnification (or resultant magnification) of the lens system must be a certain magnification as shown in FIG. 7.

Figure 1:
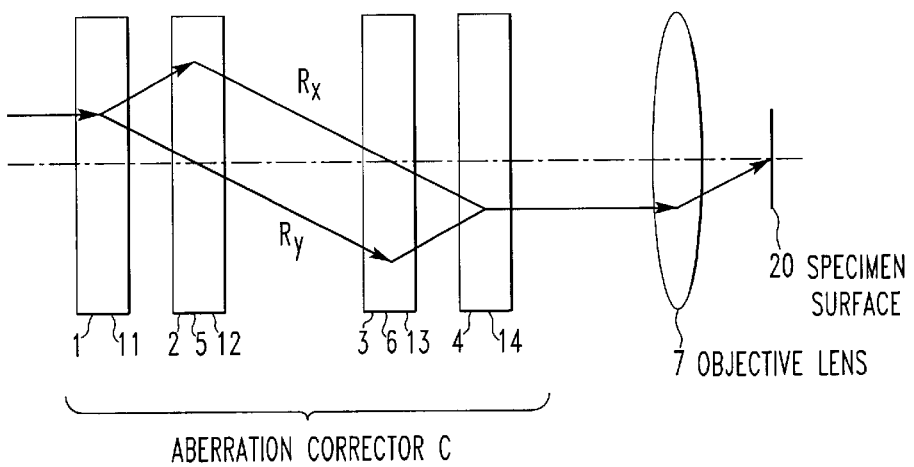
FIG. 1 is a diagram schematically illustrating the principle of an aberration corrector.
Figure 2A:
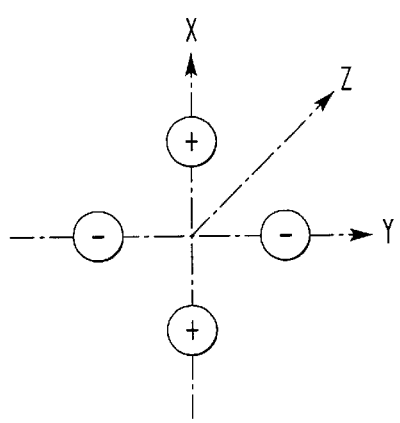
FIGS. 2(a) and 2(b) are diagrams showing a standard arrangement of electrostatic quadrupole and octupole elements.
Figure 2B:
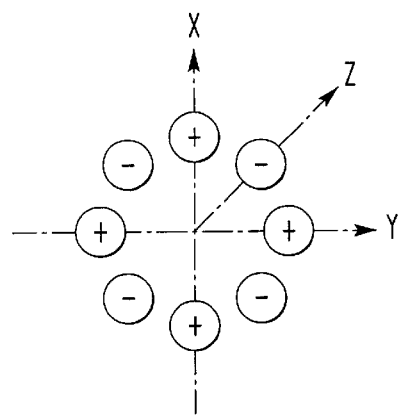

After chromatic aberration, spherical aberration, fifth-order aperture aberration, and fourth-order combined aberration of aperture and chromatic aberration are corrected in this way, if the accelerating voltage or working distance is varied, the following procedure is adopted.

Where the accelerating voltage $V_a$ is varied, the total magnification $M_t$ can be kept constant in the second embodiment. Therefore, the absolute value of the fifth-order aperture aberration coefficient can be set to a minimum value if the accelerating voltage $V_a$ is varied. Where the working distance WD is varied, the total magnification $M_t$ can be so selected that the absolute value of the fifth-order aperture aberration coefficient $C_5$ is minimized, for example, by varying the resultant magnification of the electrostatic quadrupole element 4 and objective lens 7.

Where the effects of the energy spread $\Delta V$ of the particle beam cannot be neglected at low accelerating voltage $V_a$, the fourth-order combined aberration of aperture and chromatic aberration (the amount of aberration is in proportion to the third power of the angular aperture and to the energy spread of the particle beam) may be greater than the fifth-order aperture aberration. In this case, the diffraction aberration dependent on the wavelength of the particle beam and the fourth-order combined aberration of aperture and chromatic aberration intrinsic to the lens system are dominant. It has been computationally confirmed by varying the total magnification $M_t$ of the lens system shown in FIG. 1, for example, by varying the resultant magnification of the electrostatic quadrupole element 4 and objective lens 7 that there is a magnification value $M_t=M_p$ at which the fourth-order combined aberration of aperture and chromatic aberration coefficient $C_{3c}$ converted onto the specimen surface passes through zero under conditions close to the conditions of the second embodiment.

Furthermore, calculations have proved that this magnification value $M_p$ is nearly equal to magnification value $M_O$ or slightly greater than the magnification value $M_O$ found in the previous embodiment. Where the accelerating voltage $V_a$ is varied, the total magnification $M_t$ can be kept constant in the second embodiment and so the fourth-order combined aperture and chromatic aberration coefficient $C_{3c}$ can be set to 0 or its absolute value can be set to a minimum value, if the accelerating voltage $V_a$ is varied. In addition, where the working distance WD is varied, the total magnification $M_t$ can be so selected that the fourth-order combined aperture and chromatic aberration coefficient $C_{3c}$ is set to 0 or its absolute value is set to a minimum value, for example, by varying the resultant magnification of the electrostatic quadrupole element 4 and objective lens 7.

The effects of the fourth-order combined aberration of aperture and chromatic aberration coefficient $C_{3c}$ are discussed. Where the fourth-order combined aperture and chromatic aberration coefficient $C_{3c}$ and diffraction effects are dominant, the least confusion disk of the fourth-order aperture chromatic aberration coefficient $C_{3c}$ is, in the same way as in the case of the third-order spherical aberration, given by $$d_{c3c} = \left(\frac{1}{2}\right) \cdot C_{3c} \cdot \alpha^3 \cdot \left(\frac{\Delta V}{V_a}\right) \quad (16\text{-}1)$$

where $\Delta V$ is the voltage spread corresponding to the energy spread $\Delta E$ of the electron beam. The probe diameter $d_p$ represented in terms of a root mean square is given by $$d_p = (d_\lambda^2 + d_{c3c}^2)^{1/2} \quad (16\text{-}2)$$

Therefore, from the condition $$\frac{\partial d_p}{\partial \alpha} = 0 \quad (16\text{-}3)$$

the optimum angular aperture is calculated to be $$\alpha = (1.22\lambda)^{1/4} \cdot \left(\frac{3^{1/2}}{(2 \cdot C_{3c} \cdot \Delta V / V)}\right)^{1/4} \quad (16\text{-}4)$$

The operations described above are summarized now. In the second mode (2), the aberration corrector C is so operated that the absolute values of the voltages across the electrostatic quadrupole elements are substantially uniform. At some accelerating voltage and some working distance, the total magnification $M_t$ is adjusted by varying the resultant magnification of the electrostatic quadrupole element 4 and objective lens 7 and then correction of chromatic and spherical aberrations is performed to find either a magnification value $M_t = M_O$ at which the absolute value of the fifth-order aperture aberration coefficient is minimized or a magnification value $M_t = M_P$ at which the fourth-order combined aperture and aberration coefficient is zero. If the accelerating voltage is then modified, (a) the potentials at the electrostatic quadrupole elements 2 and 3 for correction of chromatic aberration are adjusted in proportion to $V_a$ when chromatic aberration increases or decreases as a result of a modification of the accelerating voltage $V_a$. The magnetic excitations of the magnetic quadrupole elements 5 and 6 are adjusted in proportion to $V_a^{1/2}$. The potentials at the electrostatic octupole elements for correction of spherical aberration are adjusted in proportion to $V_a$. At the same time, the state of focus varies with varying the accelerating voltage $V_a$. Correspondingly, the focus potentials at the electrostatic quadrupole elements 1–4 are adjusted in proportion to the accelerating voltage $V_a$. Moreover, the objective lens 7 adjusts the focus while maintaining constant the resultant magnification of the electrostatic quadrupole element 4 and objective lens 7. As a result of these adjustments, the total magnification $M_t$ is kept at a constant magnification value $M_t = M_O$ or $M_t = M_P$. (b) On the other hand, where the working distance WD is varied, chromatic aberration increases or decreases. In response to this, the resultant magnification of the electrostatic quadrupole element 4 and objective lens 7 is adjusted. Of course, the focus on the specimen must be maintained at this time. As a result of these adjustments, the total magnification $M_t$ varies from the magnification value $M_t = M_O$ or $M_t = M_P$ that is created at the reference working distance. However, the total magnification is adjusted optimally at the working distance WD, i.e., the absolute value of the fifth-order aperture aberration is minimized or the fourth-order combined aperture and chromatic aberration coefficient is reduced to zero.

In an actual instrument, it is not always easy to know the total magnification $M_t$. Accordingly, as shown in FIG. 7, the values of the chromatic aberration-correcting potential and spherical aberration-correcting potential at which the fifth-order aperture aberration coefficient and fourth-order combined aperture and chromatic aberration coefficient are minimized are examined beforehand. The best state may be known from the actually applied values of the chromatic aberration-correcting potential and spherical aberration-correcting potential.

In the embodiments described thus far, the resultant magnification of the magnification $M_4$ of the fourth stage of electrostatic quadrupole element 4 and the magnification $M_{OL}$ of the objective lens, i.e., $$M_4 \cdot M_{OL} \quad (17)$$

is mainly adjusted, using the configuration that minimizes the number of electrooptical lenses. Thus, aberrations can be corrected over wide ranges of chromatic aberration coefficient and spherical aberration coefficient of the objective lens. However, when the magnification $M_4$ of the fourth stage of electrostatic quadrupole element 4 is varied, it is necessary to slightly vary the voltages across the quadrupole elements to obtain the reference orbit. This may increase deviations of the magnifications in the X- and Y-directions.

To alleviate this problem, at least one axially symmetrical additional lens 27 is placed between the fourth stage of electrostatic quadrupole element 4 and the objective lens 7 as shown in FIG. 8 without modifying the magnification $M_4$ of the fourth stage of quadrupole element 4. A power supply portion for the additional lens 27 is added to the power supply 17 that includes a power supply portion for the objective lens 7. The lens strength is adjusted by varying the current supplied from the power supply 17 where the additional lens 27 is of the electromagnetic type and the voltage supplied from the power supply 17 where the additional lens 27 is of the electrostatic type. It is obvious that the same advantages as produced by the embodiments above are obtained by adjusting the magnification $M_A$ of the additional lens 27. If this additional lens 27 is close to the fourth stage of electrostatic quadrupole element 4, the variable range of the resultant magnification achieved by adjusting the additional lens 27 and objective lens 7, i.e., $$M_4 \cdot M_A \cdot M_{OL} \quad (18)$$

is obviously comparable to the variable range of the resultant magnification $M_4 \cdot M_{OL}$ achieved by adjusting the fourth stage of electrostatic quadrupole element 4 and objective lens 7. Furthermore, it is clear that this additional lens can also be used to adjust the amount of aberration correction by adjusting the resultant magnification in aberration correctors other than the above embodiments. Accordingly, for convenience, the resultant magnification may be given by $$M_A \cdot M_{OL} \quad (19)$$

instead of the $M_4 \cdot M_A \cdot M_{OL}$ above.

Adjusting the resultant magnification $M_A \cdot M_{OL}$ varies the angular aperture α of the particle beam impinging on the specimen surface. As described previously in the above embodiments, the angular aperture α can be set optimally by placing an angular aperture control lens behind the objective aperture 8 or varying the diameter of the hole of the objective aperture 8 independent of adjustment of the amount of aberration correction using the additional lens 27 and objective lens 7.

In the description provided thus far, the operation of the aberration corrector cooperating either with a condenser lens system for adjusting the probe current or angular aperture or with an angular aperture control lens for adjusting the angular aperture without varying the probe current is not described in detail where the condenser lens system or angular aperture control lens is placed ahead of the corrector. Obviously, the embodiments of the present invention described above can be used where any of these lenses is placed and a control is provided.

More specifically, the main difference is that the position of the object plane relative to the first stage of electrostatic quadrupole element 1 and the angular aperture of the beam vary. The main operation consists of adjusting the focus to maintain the reference orbit by the first stage of electrostatic quadrupole element 1. Where the condenser lens system or angular aperture control lens is adjusted, the settings of the resultant magnification $M_4 \cdot M_{OL}$ or $M_4 \cdot M_A \cdot M_{OL}$ for correction of aberrations are not greatly affected.

As described thus far, an aberration corrector according to the present invention is used with an instrument utilizing a charged-particle beam and incorporated within the optics of the instrument. The corrector comprises: four stages of electrostatic quadrupole elements; two stages of magnetic quadrupole elements for superimposing a magnetic potential distribution similar to an electric potential distribution created by the two central ones of the four stages of electrostatic quadrupole elements; an objective lens; an objective aperture placed in a part of an optical path for the charged-particle beam; a manual operation-and-display portion permitting one to vary the accelerating voltage or the working distance; a power supply for supplying voltages to the four stages of electrostatic quadrupole elements, respectively; a power supply for supplying voltages to the two stages of magnetic quadrupole elements; a power supply for the objective lens; and a control portion for controlling the three power supplies according to a manual operation or setting performed on the manual operation-and-display portion.

This structure has a mode of operation in which chromatic and spherical aberrations in the particle optical system can be corrected while maintaining constant the excitations of the magnetic quadrupole elements when either the accelerating voltage or the working distance is varied. Therefore, where the excitations of the magnetic quadrupole elements are varied, magnetic drift does not occur. Furthermore, the apparatus is less affected by the magnetic variations or by voltage variations at lower accelerating voltages. Where the accelerating voltage or working distance is varied, the angular aperture of the particle beam hitting the specimen surface is automatically brought close to an optimum value.

In addition to the advantages described above, the following advantage can be had. When either the accelerating voltage or the working distance is varied, a mode of operation can be used in which at least one of chromatic and spherical aberrations in the particle optical system can be corrected under conditions where the absolute values of the voltages across the electrostatic quadrupole elements are substantially uniform or where the absolute values of the sums of the voltages across the electrostatic quadrupole elements and the voltages across the electrostatic octupole elements respectively superimposed on the former voltages are substantially uniform. Therefore, the maximum accelerating voltage can be effectively utilized. In addition, the lens system can be easily controlled where the accelerating voltage is varied.

When either the accelerating voltage or the working distance is varied, the magnification of the lens system of the particle optical system can be set to a value at which the absolute value of the fifth-order aperture aberration is minimized. Therefore, the minimum probe diameter can be always set to a minimum value.

Furthermore, when either the accelerating voltage or the working distance is varied, the magnification of the lens system of the particle optical system can be set to a value at which the absolute value of the fourth-order combined aperture and chromatic aberration is reduced to zero or a minimum. Consequently, the minimum probe diameter can be set to its minimum value at all times even at low accelerating voltages.

Moreover, where an additional lens is mounted between the objective lens and the aberration corrector and either the accelerating voltage or the working distance is varied, chromatic aberration in the whole system can be corrected by varying the resultant magnification of the additional lens and objective lens while maintaining constant the excitation current through the aberration corrector and the reference orbit within the aberration corrector. Therefore, deviations of the magnification in the X- and Y-directions can be alleviated. Additionally, it is not necessary to modify the lens magnification using the four stages of electrostatic quadrupole elements. This adjustment of the magnification needs readjustment (e.g., focus adjustment or spherical aberration) of the aberration corrector, but this is easier to perform.

Having thus described our invention with the detail and particularity required by the Patent Laws, what is desired protected by Letters Patent is set forth in the following claims.

What is claimed is:

1. An aberration corrector for use in an instrument utilizing a charged-particle beam, said aberration corrector being incorporated in optics of said instrument, said aberration corrector comprising:

four stages of electrostatic quadrupole elements including two central stages of electrostatic quadrupole elements;

two stages of magnetic quadrupole elements for superimposing a magnetic potential distribution analogous to an electric potential distribution created by said two central stages of quadrupole elements on said electric potential distribution;

an objective lens for focusing the charged-particle beam onto a specimen;

an objective aperture placed in a part of an optical path for the charged-particle beam;

a manual operation portion permitting one to modify an accelerating voltage for the charged-particle beam or a working distance between the objective lens and the specimen; and a control portion for controlling said quadrupole elements and said objective lens according to a manual operation or setting performed on said manual operation portion.

2. An aberration corrector for use in an instrument utilizing a charged-particle beam as set forth in claim 1, wherein when one of the accelerating voltage and the working distance is varied according to a manual operation or setting performed on said manual operation portion, said control portion adjusts (1) voltages applied to the electrostatic quadrupole elements and a resultant magnification of the fourth stage of electrostatic quadrupole element and the objective lens if the accelerating voltage is varied under conditions where magnetic excitations of the magnetic quadrupole elements are maintained constant and the control portion adjusts (2) the resultant magnification of the fourth stage of electrostatic quadrupole element and the objective lens if the working distance is varied under conditions where magnetic excitations of the magnetic quadrupole elements are maintained constant, whereby chromatic aberration in the optics for the charged-particle beam is corrected.

3. An aberration corrector for use in an instrument utilizing a charged-particle beam as set forth in claim 2, wherein each of said magnetic quadrupole elements is a permanent magnet.

4. An aberration corrector for use in an instrument utilizing a charged-particle beam as set forth in claim 1, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the fourth stage of electrostatic quadrupole element and the objective lens if the accelerating voltage is varied under conditions where absolute values of voltages across the four stages of electrostatic quadrupole elements are substantially uniform and the control portion adjusts (2) the resultant magnification of the fourth stage of electrostatic quadrupole element and the objective lens if the working distance is varied under conditions where absolute values of voltages across the four stages of electrostatic quadrupole elements are substantially uniform, whereby chromatic aberration in the optics for the charged-particle beam is corrected.

5. An aberration corrector for use in an instrument utilizing a charged-particle beam as set forth in claim 1, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the fourth stage of electrostatic quadrupole element and the objective lens if the accelerating voltage is varied under conditions where absolute values of voltages across the four stages of electrostatic quadrupole elements are substantially uniform and the control portion adjusts (2) the resultant magnification of the fourth stage of electrostatic quadrupole element and the objective lens if the working distance is varied under conditions where absolute values of voltages across the four stages of electrostatic quadrupole elements are substantially uniform to thereby minimize absolute value of fifth-order aperture aberration.

6. An aberration corrector for use in an instrument utilizing a charged-particle beam as set forth in claim 1, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the fourth stage of electrostatic quadrupole element and the objective lens if the accelerating voltage is varied under conditions where absolute values of voltages across the four stages of electrostatic quadrupole elements are substantially uniform and the control portion adjusts (2) the resultant magnification of the fourth stage of electrostatic quadrupole element and the objective lens if the working distance is varied under conditions where absolute values of voltages across the four stages of electrostatic quadrupole elements are substantially uniform, whereby fourth-order aperture chromatic aberration (i.e., combined aberration of third-order aperture aberration and first-order chromatic aberration) is reduced to zero or its absolute value is reduced to a minimum.

7. An aberration corrector for use in an instrument utilizing a charged-particle beam as set forth in claim 1, further comprising four stages of electrostatic octupole elements for superimposing an octupole electric potential on the electric potential distribution created by the four stages of electrostatic quadrupole elements and another control portion for controlling said four stages of electrostatic octupole elements according to a manual operation or setting performed on said manual operation portion, whereby spherical aberration can also be corrected.

8. An aberration corrector for use in an instrument utilizing a charged-particle beam as set forth in any one of claims 2 to 6, further comprising four stages of electrostatic octupole elements for superimposing an octupole electric potential on the electric potential distribution created by the four stages of electrostatic quadrupole elements and another control portion for controlling said four stages of electrostatic octupole elements according to a manual operation or setting performed on said manual operation portion, whereby spherical aberration can also be corrected.

9. An aberration corrector for use in an instrument utilizing a charged-particle beam as set forth in claim 7, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the fourth stage of electrostatic quadrupole element and the objective lens if the accelerating voltage is varied under conditions where absolute values of sums of the voltages across the electrostatic quadrupole elements and voltages across the electrostatic octupole elements respectively superimposed on the first-mentioned voltages are substantially uniform and the control portion adjusts (2) the resultant magnification of the fourth stage of electrostatic quadrupole element and the objective lens if the working distance is varied under conditions where absolute values of sums of the voltages across the electrostatic quadrupole elements and voltages across the electrostatic octupole elements respectively superimposed on the first-mentioned voltages are substantially uniform to thereby correct at least one of chromatic and spherical aberrations in the optics for the charged-particle beam.

10. An aberration corrector for use in an instrument utilizing a charged-particle beam as set forth in claim 7, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the fourth stage of electrostatic quadrupole element and the objective lens if the accelerating voltage is varied under conditions where absolute values of sums of the voltages across the four stages of electrostatic quadrupole elements and voltages across the electrostatic octupole elements respectively superimposed on the first-mentioned voltages are substantially uniform and the control portion adjusts (2) the resultant magnification of the fourth stage of electrostatic quadrupole element and the objective lens if the working distance is varied under conditions where absolute values of sums of the voltages across the four stages of electrostatic quadrupole elements and voltages across the electrostatic octupole elements respectively superimposed on the first-mentioned voltages are substantially uniform to thereby minimize absolute value of fifth-order aperture aberration.

11. An aberration corrector for use in an instrument utilizing a charged-particle beam as set forth in claim 7, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the fourth stage of electrostatic quadrupole element and the objective lens if the accelerating voltage is varied under conditions where absolute values of sums of the voltages across the four stages of electrostatic quadrupole elements and voltages across the electrostatic octupole elements respectively superimposed on the first-mentioned voltages are substantially uniform and the control portion adjusts (2) the resultant magnification of the fourth stage of electrostatic quadrupole element and the objective lens if the working distance is varied under conditions where absolute values of sums of the voltages across the four stages of electrostatic quadrupole elements and voltages across the electrostatic octupole elements respectively superimposed on the first-mentioned voltages are substantially uniform, whereby fourth-order aperture chromatic aberration (i.e., combined aberration of third-order aperture aberration and first-order chromatic aberration) is reduced to zero or its absolute value is reduced to a minimum.

12. An aberration corrector for use in an instrument utilizing a charged-particle beam, said aberration corrector being incorporated in optics of said instrument, said aberration corrector comprising:
    four stages of electrostatic quadrupole elements including two central stages of quadrupole elements;
    two stages of magnetic quadrupole elements for superimposing a magnetic potential distribution analogous to an electric potential distribution created by said two central stages of quadrupole elements on said electric potential distribution;
    an objective lens for focusing the charged-particle beam onto a specimen;
    an objective aperture placed in a part of an optical path for the charged-particle beam;
    an additional lens mounted between a quadrupole element assembly formed by said four stages of electrostatic quadrupole elements and said objective lens;
    a manual operation portion permitting one to modify an accelerating voltage for the charged-particle beam or a working distance between the objective lens and the specimen; and
    a control portion for controlling said four stages of electrostatic quadrupole elements, said two stages of magnetic quadrupole elements, said objective lens, and said additional lens according to a manual operation or setting performed on said manual operation portion.

13. An aberration corrector for use in an instrument utilizing a charged-particle beam as set forth in claim 12, wherein when one of the accelerating voltage and the working distance is varied according to a manual operation or setting performed on said manual operation portion, said control portion adjusts (1) voltages applied to the electrostatic quadrupole elements and a resultant magnification of the additional lens and the objective lens if the accelerating voltage is varied under conditions where excitations of the magnetic quadrupole elements are maintained constant and the control portion adjusts (2) the resultant magnification of the additional lens and the objective lens if the working distance is varied under conditions where excitations of the magnetic quadrupole elements are maintained constant to thereby correct chromatic aberration in the optics for the charged-particle beam.

14. An aberration corrector for use in an instrument utilizing a charged-particle beam as set forth in claim 13, wherein each of said magnetic quadrupole elements is a permanent magnet.

15. An aberration corrector for use in an instrument utilizing a charged-particle beam as set forth in claim 12, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the additional lens and the objective lens if the accelerating voltage is varied under conditions where absolute values of voltages across the four stages of electrostatic quadrupole elements are substantially uniform and the control portion adjusts (2) the resultant magnification of the and the objective lens if the working distance is varied under conditions where absolute values of voltages across the four stages of electrostatic quadrupole elements are substantially uniform to thereby correct chromatic aberration in the optics for the charged-particle beam.

16. An aberration corrector for use in an instrument utilizing a charged-particle beam as set forth in claim 12, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the additional lens and the objective lens if the accelerating voltage is varied under conditions where absolute values of voltages across the four stages of electrostatic quadrupole elements are substantially uniform and the control portion adjusts (2) the resultant magnification of the additional lens and the objective lens if the working distance is varied under conditions where absolute values of voltages across the four stages of electrostatic quadrupole elements are substantially uniform to thereby minimize absolute value of fifth-order aperture aberration.

17. An aberration corrector for use in an instrument utilizing a charged-particle beam as set forth in claim 12, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the additional lens and the objective lens if the accelerating voltage is varied under conditions where absolute values of voltages across the four stages of electrostatic quadrupole elements are substantially uniform and the control portion adjusts (2) the resultant magnification of the additional lens and the objective lens if the working distance is varied under conditions where absolute values of voltages across the four stages of electrostatic quadrupole elements are substantially uniform, whereby fourth-order aperture (i.e., combined aberration of third-order aperture aberration and first-order chromatic aberration) is reduced to zero or its absolute value is reduced to a minimum.

18. An aberration corrector for use in an instrument utilizing a charged-particle beam as set forth in claim 12, further comprising four stages of electrostatic octupole elements for superimposing an octupole electric potential on the electric potential distribution created by the four stages of electrostatic quadrupole elements and another control portion for controlling said four stages of electrostatic octupole elements according to a manual operation or setting performed on said manual operation portion, whereby spherical aberration can also be corrected.

19. An aberration corrector for use in an instrument utilizing a charged-particle beam as set forth in any one of claims 13 to 17, further comprising four stages of electrostatic octupole elements for superimposing an octupole electric potential on the electric potential distribution created by the four stages of electrostatic quadrupole elements and another control portion for controlling said four stages of electrostatic octupole elements according to a manual operation or setting performed on said manual operation portion, whereby spherical aberration can also be corrected.

20. An aberration corrector for use in an instrument utilizing a charged-particle beam as set forth in claim 18, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the additional lens and the objective lens if the accelerating voltage is varied under conditions where absolute values of sums of the voltages across the electrostatic quadrupole elements and voltages across the electrostatic octupole elements respectively superimposed on the first-mentioned voltages are substantially uniform and the control portion adjusts (2) the resultant magnification of the additional lens and the objective lens if the working distance is varied under conditions where absolute values of sums of the voltages across the electrostatic quadrupole elements and voltages across the electrostatic octupole elements respectively superimposed on the first-mentioned voltages are substantially uniform to thereby correct at least one of chromatic and spherical aberrations in the optics for the charged-particle beam.

21. An aberration corrector for use in an instrument utilizing a charged-particle beam as set forth in claim 18, wherein when one of the accelerating voltage and the working distance is varied according to a manual operation or setting performed on said manual operation portion, said control portion adjusts (1) voltages applied to the electrostatic quadrupole elements and electrical currents for exciting the magnetic quadrupole elements while maintaining constant a resultant magnification of the additional lens and the objective lens if the accelerating voltage is varied under conditions where absolute values of sums of voltages across the electrostatic quadrupole elements and voltages across the electrostatic octupole elements respectively superimposed on the first-mentioned voltages are substantially uniform and the control portion adjusts (2) the resultant magnification of the additional lens and the objective lens if the working distance is varied under conditions where absolute values of sums of voltages across the electrostatic quadrupole elements and voltages across the electrostatic octupole elements respectively superimposed on the first-mentioned voltages are substantially uniform to thereby minimize absolute value of fifth-order aperture aberration.

22. An aberration corrector for use in an instrument utilizing a charged-particle beam as set forth in claim 18, wherein when one of the accelerating voltage and the working distance is varied according to a manual operation or setting performed on said manual operation portion, said control portion adjusts (1) voltages applied to the electrostatic quadrupole elements and the electrical currents for exciting the magnetic quadrupole elements while maintaining constant a resultant magnification of the additional lens and the objective lens if the accelerating voltage is varied under conditions where absolute values of sums of voltages across the electrostatic quadrupole elements and voltages across the electrostatic octupole elements respectively superimposed on the first-mentioned voltages are substantially uniform and the control portion adjusts (2) the resultant magnification of the additional lens and the objective lens if the working distance is varied under conditions where absolute values of sums of voltages across the electrostatic quadrupole elements and voltages across the electrostatic octupole elements respectively superimposed on the first-mentioned voltages are substantially uniform, whereby fourth-order aperture chromatic aberration (i.e., combined aberration of third-order aperture aberration and first-order chromatic aberration) is reduced to zero or its absolute value is reduced to a minimum.

23. An aberration corrector for use in an instrument utilizing a charged-particle beam as set forth in any one of claims 1 and 12, wherein said control portion sets electric potentials at said two central stages of electrostatic quadrupole elements for correcting chromatic aberration to their preset values and then performs correction of chromatic aberration, whereby absolute value of fifth-order aperture aberration is minimized or fourth-order aperture chromatic aberration (i.e., combined aberration of third-order aperture aberration and first-order chromatic aberration) is reduced to zero or its absolute value is reduced to a minimum.

24. An aberration corrector for use in an instrument utilizing a charged-particle beam as set forth in any one of claims 7 and 18, wherein said control portion sets electric potentials at said two central stages of electrostatic quadrupole elements for correcting chromatic aberration and electric potentials at the four stages of electrostatic octupole elements for correcting spherical aberration to their preset values and then performs correction of chromatic and spherical aberrations, whereby absolute value of fifth-order aperture aberration is minimized or fourth-order aperture chromatic aberration (i.e., combined aberration of third-order aperture aberration and first-order chromatic aberration) is reduced to zero or its absolute value is reduced to a minimum.

* * * * *

UNITED STATES PATENT AND TRADEMARK OFFICE
CERTIFICATE OF CORRECTION

PATENT NO. : 6,723,997 B2
DATED : April 20, 2004
INVENTOR(S) : Matsuya et al.

It is certified that error appears in the above-identified patent and that said Letters Patent is hereby corrected as shown below:

Title page,
Item [73], Assignee, "Jeol Ltd." should read -- JEOL Ltd. --.
Item [56], References Cited, OTHER PUBLICATIONS, "SEM by a multiple" should read -- SEM by a multipole --.

Column 26,
Line 34, "of the and the" should read -- of the additional lens and the --.

Signed and Sealed this

Fifth Day of October, 2004

JON W. DUDAS
*Director of the United States Patent and Trademark Office*